United States Patent
Durrani (10) Patent No.: US 10,137,284 B2
(45) Date of Patent: Nov. 27, 2018

(54) PLEURAL SPACE DRAINING ASSEMBLY

(71) Applicant: Jameel Durrani, Center Valley, PA (US)

(72) Inventor: Jameel Durrani, Center Valley, PA (US)

( * ) Notice: Subject to any disclaimer, the term of this patent is extended or adjusted under 35 U.S.C. 154(b) by 241 days.

(21) Appl. No.: 15/350,880

(22) Filed: Nov. 14, 2016

(65) Prior Publication Data

US 2018/0133445 A1 May 17, 2018

(51) Int. Cl.

| | |
|---|---|
| *A61M 27/00* | (2006.01) |
| *A61M 1/00* | (2006.01) |
| *A61M 25/10* | (2013.01) |
| *A61M 39/22* | (2006.01) |
| *A61M 25/02* | (2006.01) |
| *A61B 1/05* | (2006.01) |
| *A61B 1/06* | (2006.01) |

(52) U.S. Cl.
CPC ............... *A61M 27/00* (2013.01); *A61B 1/05* (2013.01); *A61B 1/0661* (2013.01); *A61M 1/008* (2013.01); *A61M 25/02* (2013.01); *A61M 25/10* (2013.01); *A61M 39/22* (2013.01); *A61M 2025/024* (2013.01); *A61M 2025/0266* (2013.01); *A61M 2027/004* (2013.01); *A61M 2205/32* (2013.01)

(58) Field of Classification Search
CPC .... A61M 27/00; A61M 25/10; A61M 25/007; A61M 25/0071; A61M 2025/0063; A61M 2025/0095; A61M 2210/101; A61M 25/0102; A61M 1/008

See application file for complete search history.

(56) References Cited

U.S. PATENT DOCUMENTS

| 3,542,026 | A | 11/1970 | Bledsoe | |
|---|---|---|---|---|
| 5,370,610 | A | 12/1994 | Reynolds | |
| 5,637,091 | A * | 6/1997 | Hakky | A61M 25/0017 604/528 |
| 5,693,030 | A * | 12/1997 | Lee | A61M 25/0068 604/117 |
| 6,299,593 | B1 | 10/2001 | Wakabayashi | |
| D498,844 | S | 11/2004 | Diamond et al. | |
| 7,695,467 | B2 | 4/2010 | Breznock et al. | |
| 8,992,493 | B2 | 3/2015 | Croteau et al. | |
| 2003/0078562 | A1* | 4/2003 | Makower | A61B 17/12109 604/509 |
| 2004/0078026 | A1* | 4/2004 | Wagner | A61M 27/00 604/541 |

(Continued)

*Primary Examiner* — Susan Su (57) ABSTRACT

A pleural space draining assembly for draining gas and liquid from a pleural space includes a catheter. Walls, coupled to and positioned in the catheter, define a first channel, a second channel, and a third channel. A first port, fluidically coupled to the first channel, is positioned through the catheter proximate to a first end of the catheter. A stylet, which has a tip that is blunt, is complementary to the first channel. A second port, fluidically coupled to the second channel, is positioned through the catheter between the first port and a midpoint of the catheter. A balloon is sealably positioned in the second channel. The balloon is configured to reversibly and selectively inflate. Holes, fluidically coupled to the third channel, are positioned through the catheter. A valve is fluidically coupled to the third channel at the first end of the catheter.

20 Claims, 5 Drawing Sheets

(56) References Cited

U.S. PATENT DOCUMENTS

| | | | |
|---|---|---|---|
| 2008/0200834 A1* | 8/2008 | Mark | A61B 17/3403 600/566 |
| 2013/0190562 A1* | 7/2013 | Smith | A61B 1/018 600/107 |
| 2015/0018606 A1* | 1/2015 | Ariura | A61M 25/0023 600/37 |
| 2015/0051634 A1* | 2/2015 | Kravik | A61B 17/12109 606/194 |
| 2016/0220786 A1* | 8/2016 | Mitchell | A61M 25/0029 |
| 2016/0249978 A1* | 9/2016 | Lee | A61B 1/3137 600/476 |

* cited by examiner

PLEURAL SPACE DRAINING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art including information disclosed under 37 CFR 1.97 and 1.98

The disclosure and prior art relates to draining assemblies and more particularly pertains to a new draining assembly for draining gas and liquid from a pleural space.

BRIEF SUMMARY OF THE INVENTION

An embodiment of the disclosure meets the needs presented above by generally comprising a catheter. A plurality of walls is coupled to and positioned in the catheter. The walls define a first channel, a second channel, and a third channel. A first port is positioned through the catheter proximate to a first end of the catheter. The first port is fluidically coupled to the first channel. A stylet, which has a tip that is blunt is complementary to the first channel. A second port is positioned through the catheter between the first port and a midpoint of the catheter. The second port is fluidically coupled to the second channel. A balloon is sealably positioned in the second channel with an open end protruding from the first end of the catheter. The balloon is configured to reversibly and selectively inflate. A plurality of holes, fluidically coupled to the third channel, is positioned through the catheter. A valve is fluidically coupled to the third channel at the first end of the catheter.

The first port is positioned insert the stylet into the first channel so that the catheter is configured to insert into a pleural space of a patient. The balloon is configured for inflation such that an inflated portion of the balloon protrudes from the catheter to fixedly position the catheter between a lung and an internal chest wall of the patient. The holes are configured for gas and fluid to enter the third channel. The valve is configured to couple to an accessory utilized in removing air and liquid from the pleural space through the third channel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
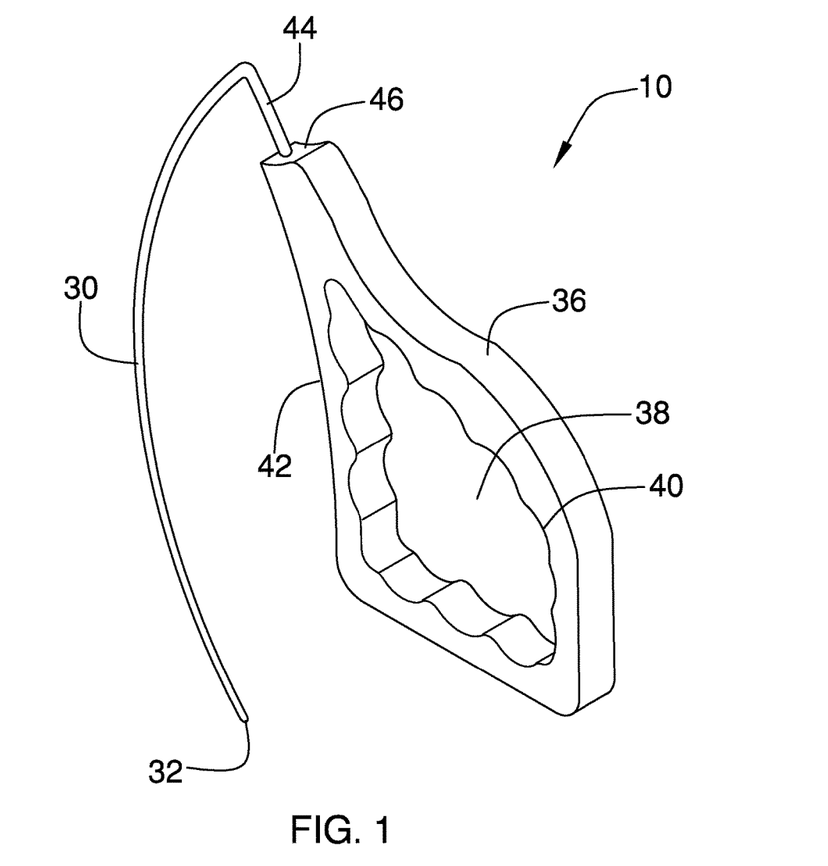
FIG. 1 is an isometric perspective view of a pleural space draining assembly according to an embodiment of the disclosure.
Figure 2:
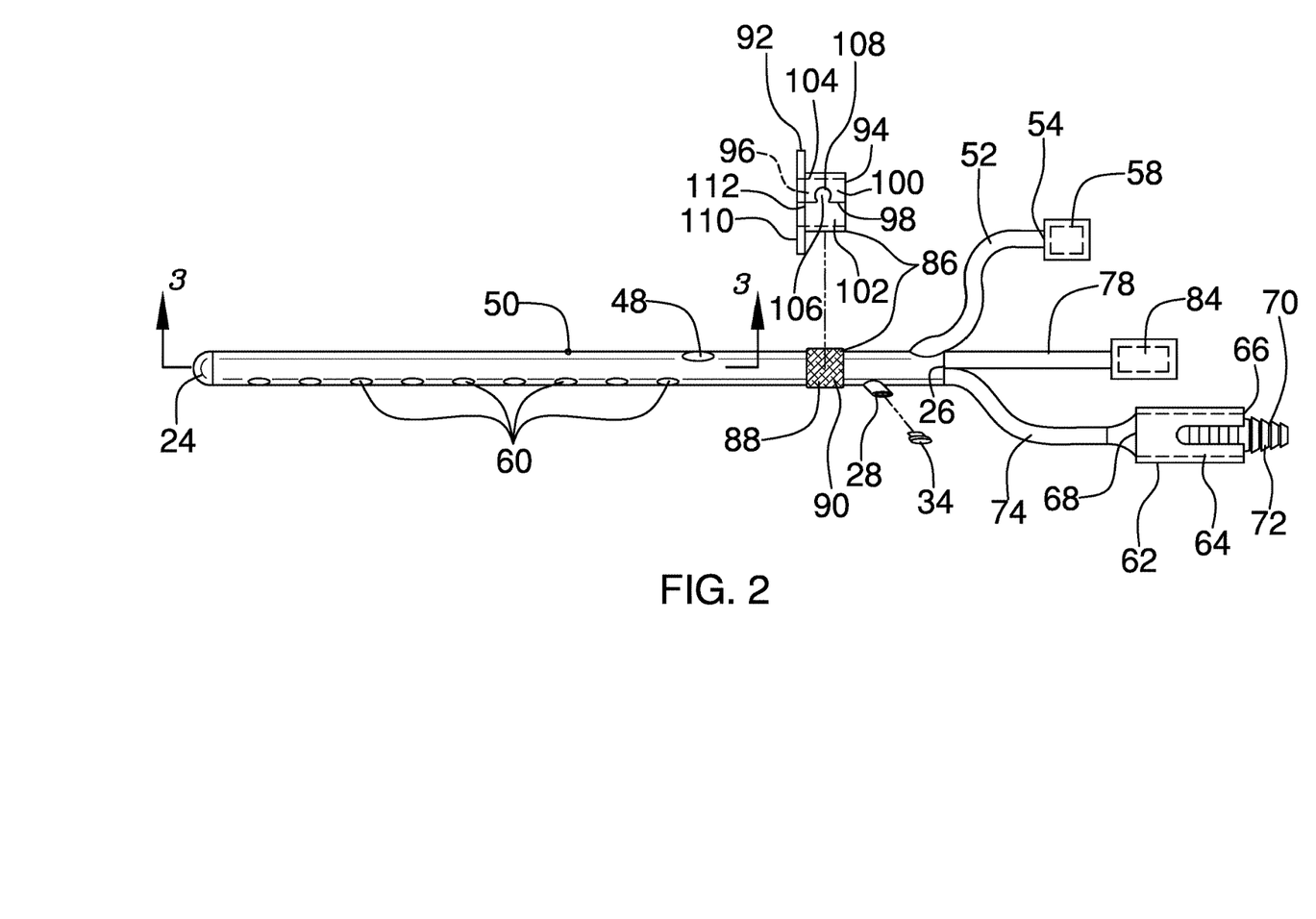
FIG. 2 is a side view of an embodiment of the disclosure.
Figures 3, 4:
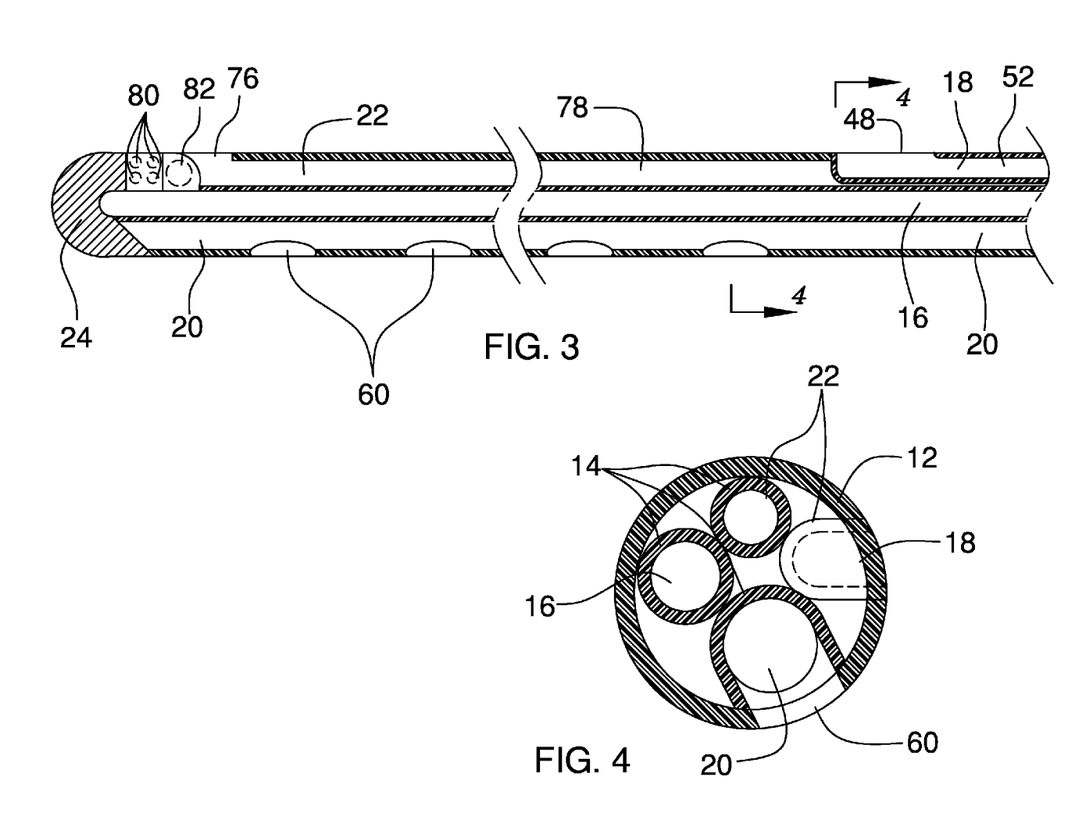
FIG. 3 is a cross-sectional view of an embodiment of the disclosure.
FIG. 4 is a cross-sectional view of an embodiment of the disclosure.
Figure 5:
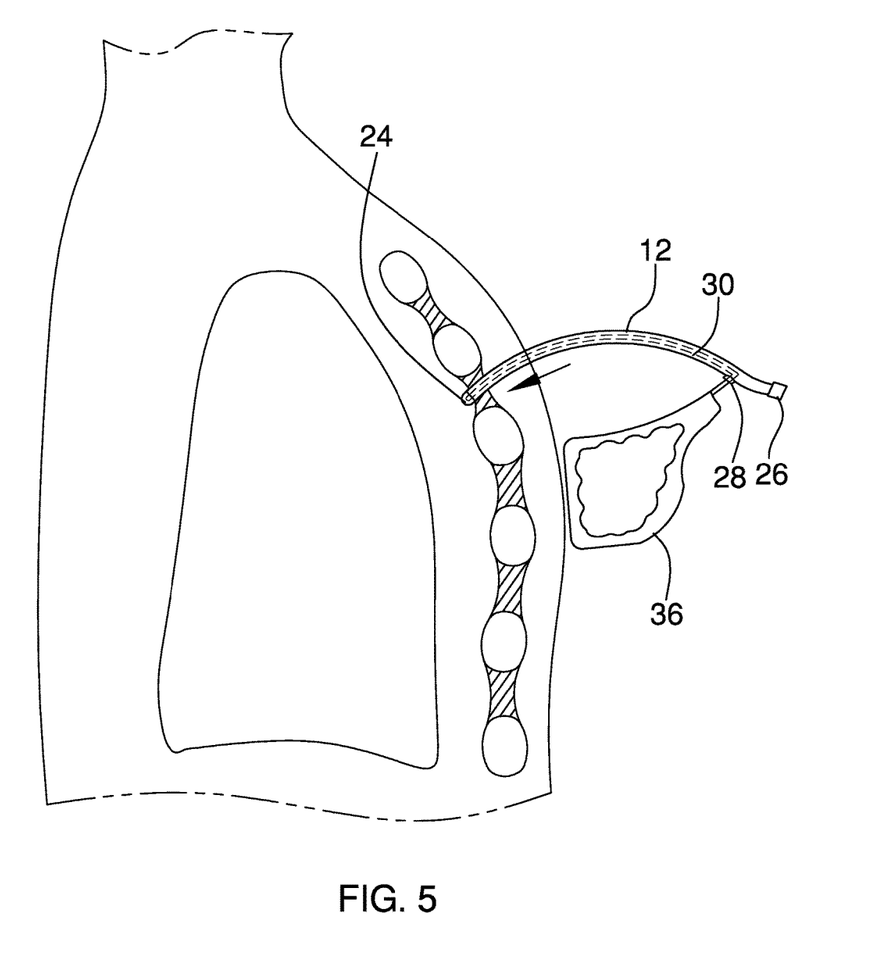
FIG. 5 is an in-use view of an embodiment of the disclosure.
Figure 6:
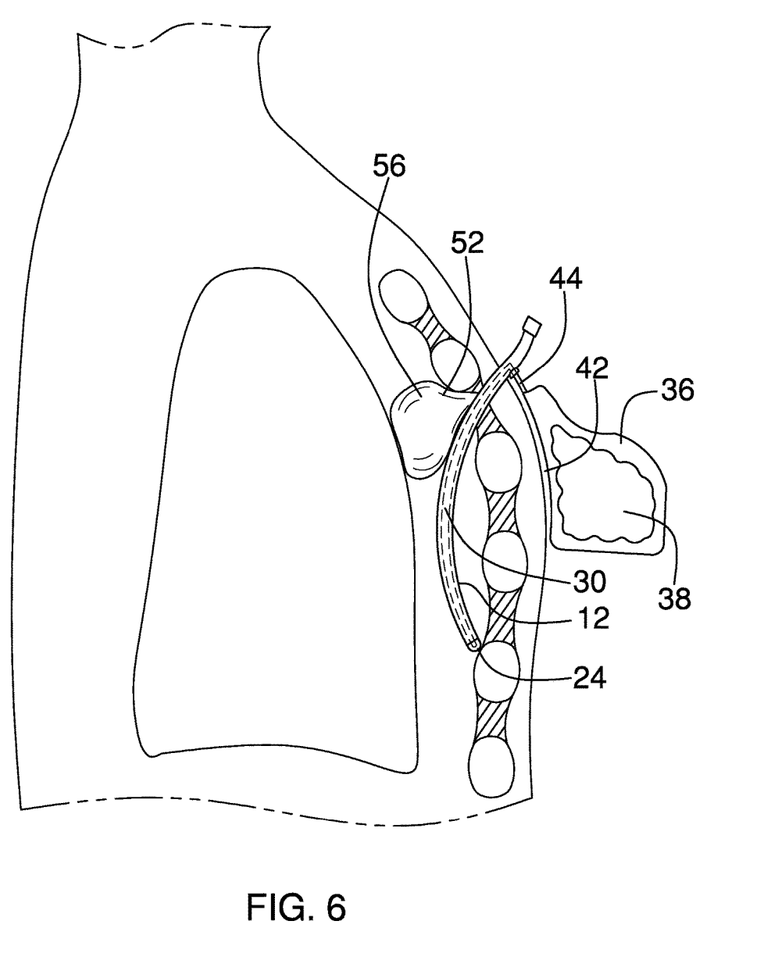
FIG. 6 is an in-use view of an embodiment of the disclosure.

With reference now to the drawings, and in particular to FIGS. 1 through 6 thereof, a new draining assembly embodying the principles and concepts of an embodiment of the disclosure and generally designated by the reference numeral 10 will be described.

As best illustrated in FIGS. 1 through 6, the pleural space draining assembly 10 generally comprises a catheter 12. The catheter 12 comprises latex that is medical grade. A plurality of walls 14 is coupled to and positioned in the catheter 12. The walls 14 define a first channel 16, a second channel 18, a third channel 20 and a fourth channel 22 within the catheter 12. The first channel 16, the third channel 20 and the fourth channel 22 extend to proximate to a second end 24 of the catheter 12. The fourth channel 22 and the second end 24 of the catheter 12 are radiopaque. The second channel 18, the third channel 20 and the fourth channel 22 are open at a first end 26 of the catheter 12.

A first port 28 is positioned through the catheter 12 proximate to the first end 26 of the catheter 12. The first port 28 is fluidically coupled to the first channel 16. In one embodiment, the first port 28 protrudes angularly from the catheter 12.

The assembly 10 comprises a stylet 30 that has a tip 32, which is blunt. The stylet 30 is complementary to the first channel 16. The first port 28 is positioned in the catheter 12 such that the first port 28 is positioned to insert the stylet 30 into the first channel 16. The catheter 12 is configured to insert into a pleural space of a patient. In one embodiment, the stylet 30 is arcuate.

The assembly 10 comprises a cap 34 that is complementary to the first port 28. The cap 34 is reversibly couplable to the catheter 12 to selectively closed the first port 28. The cap 34 is positioned to couple to the catheter 12 to close the first port 28 when the stylet 30 is withdrawn from the second channel 18.

A handle 36 is coupled to the stylet 30 distal from the tip 32. In one embodiment, the handle 36 is substantially b-shaped and defines a grasp 38. The grasp 38 is positioned in the handle 36 such that the grasp 38 is configured to insert a least a portion of a hand of a user to clasp the handle 36. The grasp 38 has an internal perimeter 40. In another embodiment, the internal perimeter 40 is contoured. In yet another embodiment, the handle 36 has a side 42 that is opposingly positioned to the stylet 30. The side 42 is concavely arcuate such that the side 42 is substantially complementary to an external chest wall of the patient.

In one embodiment, an extension 44 is coupled to and positioned between the stylet 30 and a top end 46 of the handle 36. The extension 44 is positioned on the handle 36 such that the stylet 30 is opposingly positioned to the side 42 of the handle 36.

A second port 48 is positioned through the catheter 12 between the first port 28 and a midpoint 50 of the catheter 12. The second port 48 is fluidically coupled to the second channel 18. The second channel 18 extends from the first end 26 to the second port 48.

A balloon 52 is sealably positioned in the second channel 18. The balloon 52 has an open end 54 that protrudes from the first end 26 of the catheter 12. The balloon 52 is configured to reversibly and selectively inflate. The balloon 52 is positioned in the second channel 18 such that the balloon 52 is configured to inflate. An inflated portion 56 of the balloon 52 protrudes from the catheter 12 to fixedly position the catheter 12 between a lung and an internal chest wall of the patient. In one embodiment, a first connector 58 is coupled to the open end 54 of the balloon 52. The first connector 58 is positioned on the balloon 52 such that the first connector 58 is configured to couple the balloon 52 to an inflating device.

A plurality of holes 60 is positioned through the catheter 12. The holes 60 are fluidically coupled to the third channel 20. The holes 60 are positioned in the catheter 12 such that the holes 60 are configured to allow gas and fluid to enter the third channel 20. In one embodiment, the plurality of holes 60 extends substantially linearly from proximate to the second end 24 of the catheter 12. In another embodiment, the plurality of holes 60 extends to proximate to the second port 48. In yet another embodiment, the plurality of holes 60 comprises from four to nine holes 60.

A valve 62 is fluidically coupled to the third channel 20 at the first end 26 of the catheter 12. The valve 62 is positioned on the catheter 12 such that the valve 62 is configured to couple to an accessory. The accessory is utilized in removing air and liquid from the pleural space through the third channel 20. The valve 62 is configured to prevent entry and exit of gas and liquid through the third channel 20 when the valve 62 is not coupled to the accessory.

In one embodiment, the valve 62 comprises a shell 64 that is tubular. The shell 64 has a first endpoint 66 and a second endpoint 68. The first endpoint 66 is fluidically coupled to the third channel 20. The second endpoint 68 is open. A funicular cone 70 is positioned through the second endpoint 68 and is rotationally coupled to the shell 64. The funicular cone 70 has an outer surface 72 that is ridged. The funicular cone 70 is positioned on the shell 64 such that the funicular cone 70 is configured to rotationally couple to the accessory to couple the valve 62 to the accessory with concurrent opening of the valve 62. Rotational decoupling of the funicular cone 70 from the accessory closes the valve 62.

In one embodiment, a tube 74 is coupled and extends between the first end 26 of the catheter 12 and the valve 62. The tube 74 is fluidically coupled to the third channel 20 and the valve 62. The valve 62 is thus flexibly connected to the third channel 20.

A third port 76 is positioned through the catheter 12 proximate to the second end 24. The third port 76 is fluidically coupled to the fourth channel 22. The third port 76 is positioned through the catheter 12 such that the fourth channel 22 is configured to insert interventional instruments through the fourth channel 22 into the chest cavity of the patient.

In one embodiment, a cable 78 is positioned in the fourth channel 22. The cable 78 extends from proximate to the second end 24 to protrude through the first end 26 of the catheter 12. A light 80 and a camera 82 are coupled to and positioned in the catheter 12 proximate to the second end 24. The light 80 and the camera 82 are operationally coupled to the cable 78. In one embodiment, the light 80 is fiber optic. A second connector 84 is coupled to the cable 78 distal from the light 80 and the camera 82. The second connector 84 is positioned on the cable 78 such that the second connector 84 is configured to couple the light 80 and the camera 82 to a visualizing device.

A stabilizer 86 is couplable to the catheter 12 between the first port 28 and the second port 48. The stabilizer 86 is configured to suturelessly stabilize the catheter 12 within the pleural cavity of the patient. In one embodiment, the stabilizer 86 comprises an adhesive strip 88 that is selectively couplable to the catheter 12 between the first port 28 and the second port 48. The adhesive strip 88 has an outer layer 90 that is coarse. A clamp 92, which is complementary to the catheter 12, is reversibly positionable around the catheter 12 and frictionally couplable to the adhesive strip 88. The clamp 92 is abuttingly positioned against the exterior chest wall of the patient to stabilize the catheter 12 within the pleural cavity of the patient.

In another embodiment, the clamp 92 comprises a pipe 94. The pipe 94 comprises plastic such that the pipe 94 is deformable. The pipe 94 is perforated longitudinally on a back face 96. A slit 98 is positioned longitudinally through a front face 100 of the pipe 94 and defines a first section 102 and second section 104 of the pipe 94. A tab 106 is coupled to and extends from the first section 102. A cutout 108 is positioned in the second section 104. The cutout 108 is complementary to the tab 106. A flange 110 is coupled to and extends radially from a terminus 112 of the pipe 94. The cutout 108 is positioned in the second section 104 such that the cutout 108 is positioned to insert the tab 106 to couple the second section 104 to the first section 102, such that the clamp 92 is coupled to the catheter 12. The flange 110 is abuttingly positioned against the exterior chest wall of the patient to stabilize the catheter 12 within the pleural cavity of the patient.

In use, the first port 28 is positioned to insert the stylet 30 into the first channel 16. The catheter 12 is configured to insert into the pleural space of the patient. The balloon 52 is configured to inflate such that the inflated portion 56 of the balloon 52 protrudes from the catheter 12 to fixedly position the catheter 12 between the lung and the internal chest wall of the patient. The clamp 92 is abuttingly positioned against the exterior chest wall of the patient to stabilize the catheter 12 within the pleural cavity of the patient. The holes 60 that are positioned in the catheter 12 are configured for gas and fluid to enter the third channel 20. The valve 62 is configured to couple to the accessory utilized in removing air and liquid from the pleural space through the third channel 20. The third port 76 that is positioned through the catheter 12 is configured to insert interventional instruments through the fourth channel 22 into the chest cavity of the patient.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pleural space draining assembly comprising:
   a catheter;
   a plurality of walls coupled to and positioned in said catheter defining a first channel, a second channel, and a third channel within said catheter;
   a first port positioned through said catheter proximate to a first end of said catheter, said first port being fluidically coupled to said first channel;
   a stylet having a tip, said tip being blunt, said stylet being complementary to said first channel;
   a second port positioned through said catheter between said first port and a midpoint of said catheter, said second port being fluidically coupled to said second channel;
   a balloon sealably positioned in said second channel, said balloon having an open end protruding from said first end of said catheter, said balloon being configured for reversible and selective inflation;
   a plurality of holes positioned through said catheter, said holes being fluidically coupled to said third channel;
   a valve fluidically coupled to said third channel at said first end of said catheter; and
   wherein said first port is positioned in said catheter such that said first port is positioned for insertion of said stylet into said first channel, wherein said catheter is configured for insertion into a pleural space of a patient, wherein said balloon is positioned in said second channel such that said balloon is configured for inflation such that an inflated portion of said balloon protrudes from said catheter to fixedly position said catheter between a lung and an internal chest wall of the patient, wherein said holes are positioned in said catheter such that said holes are configured for gas and fluid to enter said third channel, and wherein said valve is positioned on said catheter such that said valve is configured for coupling to an accessory utilized in removing air and liquid from the pleural space through said third channel.

2. The assembly of claim 1, further including said catheter comprising latex, said latex being medical grade.

3. The assembly of claim 1, further comprising:
   said first channel and said third channel extending to proximate to a second end of said catheter;
   said second channel extending from said first end to said second port;
   said second channel, said third channel and said fourth channel being open at said first end of said catheter;
   said first port protruding angularly from said catheter; and
   said stylet being arcuate.

4. The assembly of claim 1, further including a cap complementary to said first port, said cap being reversibly couplable to said catheter to selectively closed said first port, wherein said cap is positioned to couple to said catheter to close said first port when said stylet is withdrawn from said second channel.

5. The assembly of claim 1, further including a handle coupled to said stylet distal from said tip.

6. The assembly of claim 5, further including said handle being substantially b-shaped defining a grasp, wherein said grasp is positioned in said handle such that said grasp is configured for insertion of a least a portion of a hand of a user to clasp said handle.

7. The assembly of claim 6, further including said grasp having an internal perimeter, said internal perimeter being contoured.

8. The assembly of claim 5, further comprising:
   said handle having a side, said side being opposingly positioned to said stylet, said side being concavely arcuate such that said side is substantially complementary to an external chest wall of the patient;
   an extension coupled to and positioned between said stylet and a top end of said handle; and
   wherein said extension is positioned on said handle such that said stylet is opposingly positioned to said side of said handle.

9. The assembly of claim 1, further including a first connector coupled to said open end of said balloon, wherein said first connector is positioned on said balloon such that said first connector is configured to couple said balloon to an inflating device.

10. The assembly of claim 1, further including said plurality of holes extending substantially linearly from proximate to a second end of said catheter.

11. The assembly of claim 10, further including said plurality of holes extending to proximate to said second port.

12. The assembly of claim 10, further including said plurality of holes comprising from four to nine said holes.

13. The assembly of claim 1, further including said valve being configured to prevent entry and exit of gas and liquid through said third channel when said valve is not coupled to the accessory.

14. The assembly of claim 13, further including said valve comprising:
   a shell, said shell being tubular, said shell having a first endpoint and a second endpoint, said first endpoint being fluidically coupled to said third channel, said second endpoint being open;

a funicular cone positioned through said second endpoint and rotationally coupled to said shell, said funicular cone having an outer surface, said outer surface being ridged; and wherein said funicular cone is positioned on said shell such that said funicular cone is configured for rotational coupling to the accessory to couple said valve to the accessory with concurrent opening of said valve, and wherein rotational decoupling of said funicular cone from the accessory closes said valve.

15. The assembly of claim 13, further including a tube coupled and extending between said first end of said catheter and said valve, said tube being fluidically coupled to said third channel and said valve such that said valve is flexibly connected to said third channel.

16. The assembly of claim 1, further comprising:
said plurality of walls defining a fourth channel within said catheter, said fourth channel extending to proximate to a second end of said catheter, said fourth channel and said second end of said catheter being radiopaque, said fourth channel being open at said first end of said catheter;
a third port positioned through said catheter proximate to said second end, said third port being fluidically coupled to said fourth channel, wherein said third port is positioned through said catheter such that said fourth channel is configured for insertion of interventional instruments through said fourth channel into the chest cavity of the patient;
a cable positioned in said fourth channel, said cable extending from proximate to said second end to protrude through said first end of said catheter;
a light coupled to and positioned in said catheter proximate to said second end, said light being operationally coupled to said cable, said light being fiber optic,
a camera coupled to and positioned in said catheter proximate to said light, said camera being operationally coupled to said cable;
a second connector coupled to said cable distal from said light and said camera; and
wherein said second connector is positioned on said cable such that said second connector is configured to couple said light and said camera to a visualizing device.

17. The assembly of claim 1, further including a stabilizer couplable to said catheter between said first port and said second port, said stabilizer being configured to suturelessly stabilize said catheter within the pleural cavity of the patient.

18. The assembly of claim 17, further including said stabilizer comprising:
an adhesive strip selectively coupled to said catheter between said first port and said second port, said adhesive strip having an outer layer, said outer layer being coarse;
a clamp complementary to said catheter, said clamp being reversibly positionable around said catheter and frictionally couplable to said adhesive strip; and
wherein said clamp is abuttingly positioned against the exterior chest wall of the patient to stabilize said catheter within the pleural cavity of the patient.

19. The assembly of claim 18, further including said clamp comprising:
a pipe, said pipe comprising plastic such that said pipe is deformable, said pipe being longitudinally perforated on a back face;
a slit positioned longitudinally through a front face of said pipe defining a first section and second section of said pipe;

a tab coupled to and extending from said first section;
a cutout positioned in said second section, said cutout being complementary to said tab;
a flange coupled to and extending radially from a terminus of said pipe; and
wherein said cutout is positioned in said second section such that said cutout is positioned for insertion of said tab to couple said second section to said first section such that said clamp is coupled to said catheter, wherein said flange is abuttingly positioned against the exterior chest wall of the patient to stabilize said catheter within the pleural cavity of the patient.

20. A pleural space draining assembly comprising:
a catheter, said catheter comprising latex, said latex being medical grade;
a plurality of walls coupled to and positioned in said catheter defining a first channel, a second channel, a third channel and a fourth channel within said catheter, said first channel, said third channel and said fourth channel extending to proximate to a second end of said catheter, said fourth channel and said second end of said catheter being radiopaque, said second channel, said third channel and said fourth channel being open at a first end of said catheter;
a first port positioned through said catheter proximate to said first end of said catheter, said first port being fluidically coupled to said first channel, said first port protruding angularly from said catheter;
a stylet having a tip, said tip being blunt, said stylet being complementary to said first channel, wherein said first port is positioned in said catheter such that said first port is positioned for insertion of said stylet into said first channel, wherein said catheter is configured for insertion into a pleural space of a patient, said stylet being arcuate;
a cap complementary to said first port, said cap being reversibly couplable to said catheter to selectively closed said first port, wherein said cap is positioned to couple to said catheter to close said first port when said stylet is withdrawn from said second channel;
a handle coupled to said stylet distal from said tip, said handle being substantially b-shaped defining a grasp, wherein said grasp is positioned in said handle such that said grasp is configured for insertion of a least a portion of a hand of a user to clasp said handle, said grasp having an internal perimeter, said internal perimeter being contoured, said handle having a side, said side being opposingly positioned to said stylet, said side being concavely arcuate such that said side is substantially complementary to an external chest wall of the patient;
an extension coupled to and positioned between said stylet and a top end of said handle, wherein said extension is positioned on said handle such that said stylet is opposingly positioned to said side of said handle;
a second port positioned through said catheter between said first port and a midpoint of said catheter, said second port being fluidically coupled to said second channel, said second channel extending from said first end to said second port;
a balloon sealably positioned in said second channel, said balloon having an open end protruding from said first end of said catheter, said balloon being configured for reversible and selective inflation, wherein said balloon is positioned in said second channel such that said balloon is configured for inflation such that an inflated portion of said balloon protrudes from said catheter to fixedly position said catheter between a lung and an internal chest wall of the patient;

a first connector coupled to said open end of said balloon, wherein said first connector is positioned on said balloon such that said first connector is configured to couple said balloon to an inflating device;

a plurality of holes positioned through said catheter, said holes being fluidically coupled to said third channel, wherein said holes are positioned in said catheter such that said holes are configured for gas and fluid to enter said third channel, said plurality of holes extending substantially linearly from proximate to said second end of said catheter, said plurality of holes extending to proximate to said second port, said plurality of holes comprising from four to nine said holes;

a valve fluidically coupled to said third channel at said first end of said catheter, wherein said valve is positioned on said catheter such that said valve is configured for coupling to an accessory utilized in removing air and liquid from the pleural space through said third channel, said valve being configured to prevent entry and exit of gas and liquid through said third channel when said valve is not coupled to the accessory, said valve comprising:
 a shell, said shell being tubular, said shell having a first endpoint and a second endpoint, said first endpoint being fluidically coupled to said third channel, said second endpoint being open, and
 a funicular cone positioned through said second endpoint and rotationally coupled to said shell, said funicular cone having an outer surface, said outer surface being ridged, wherein said funicular cone is positioned on said shell such that said funicular cone is configured for rotational coupling to the accessory to couple said valve to the accessory with concurrent opening of said valve, and wherein rotational decoupling of said funicular cone from the accessory closes said valve;

a tube coupled and extending between said first end of said catheter and said valve, said tube being fluidically coupled to said third channel and said valve such that said valve is flexibly connected to said third channel;

a third port positioned through said catheter proximate to said second end, said third port being fluidically coupled to said fourth channel, wherein said third port is positioned through said catheter such that said fourth channel is configured for insertion of interventional instruments through said fourth channel into the chest cavity of the patient;

a cable positioned in said fourth channel, said cable extending from proximate to said second end to protrude through said first end of said catheter;

a light coupled to and positioned in said catheter proximate to said second end, said light being operationally coupled to said cable, said light being fiber optic;

a camera coupled to and positioned in said catheter proximate to said light, said camera being operationally coupled to said cable;

a second connector coupled to said cable distal from said light and said camera, wherein said second connector is positioned on said cable such that said second connector is configured to couple said light and said camera to a visualizing device;

a stabilizer couplable to said catheter between said first port and said second port, said stabilizer being configured to sutureles sly stabilize said catheter within the pleural cavity of the patient, said stabilizer comprising:
 an adhesive strip selectively coupled to said catheter between said first port and said second port, said adhesive strip having an outer layer, said outer layer being coarse, and
 a clamp complementary to said catheter, said clamp being reversibly positionable around said catheter and frictionally couplable to said adhesive strip, wherein said clamp is abuttingly positioned against the exterior chest wall of the patient to stabilize said catheter within the pleural cavity of the patient, said clamp comprising:
  a pipe, said pipe comprising plastic such that said pipe is deformable, said pipe being longitudinally perforated on a back face,
  a slit positioned longitudinally through a front face of said pipe defining a first section and second section of said pipe,
  a tab coupled to and extending from said first section,
  a cutout positioned in said second section, said cutout being complementary to said tab,
  a flange coupled to and extending radially from a terminus of said pipe, and
  wherein said cutout is positioned in said second section such that said cutout is positioned for insertion of said tab to couple said second section to said first section such that said clamp is coupled to said catheter, wherein said flange is abuttingly positioned against the exterior chest wall of the patient to stabilize said catheter within the pleural cavity of the patient; and wherein said first port is positioned in said catheter such that said first port is positioned for insertion of said stylet into said first channel, wherein said catheter is configured for insertion into the pleural space of the patient, wherein said balloon is positioned in said second channel such that said balloon is configured for inflation such that the inflated portion of said balloon protrudes from said catheter to fixedly position said catheter between the lung and the internal chest wall of the patient, wherein said clamp is abuttingly positioned against the exterior chest wall of the patient to stabilize said catheter within the pleural cavity of the patient, wherein said holes are positioned in said catheter such that said holes are configured for gas and fluid to enter said third channel, wherein said valve is positioned on said catheter such that said valve is configured for coupling to the accessory utilized in removing air and liquid from the pleural space through said third channel, and wherein said third port is positioned through said catheter such that said fourth channel is configured for insertion of interventional instruments through said fourth channel into the chest cavity of the patient.

* * * * *